United States Patent
Nugent, Jr.

(10) Patent No.: US 6,207,847 B1
(45) Date of Patent: Mar. 27, 2001

(54) MANUFACTURE OF OPTICALLY ACTIVE HALOHYDRIN TRIALKYLSILYL ETHERS

(75) Inventor: William Aloysius Nugent, Jr., Cherry Hill, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/462,973

(22) PCT Filed: Jul. 8, 1998

(86) PCT No.: PCT/US98/14068

§ 371 Date: Jan. 14, 2000

§ 102(e) Date: Jan. 14, 2000

(87) PCT Pub. No.: WO99/02535

PCT Pub. Date: Jan. 21, 1999

Related U.S. Application Data
(60) Provisional application No. 60/052,196, filed on Jul. 10, 1997.

(51) Int. Cl.[7] ................ C07F 7/08; C07F 7/18
(52) U.S. Cl. ................................ 556/470
(58) Field of Search ........................ 556/470

(56) References Cited

U.S. PATENT DOCUMENTS 5,231,203 * 7/1993 Nugent ............... 556/470 X
5,821,307 * 10/1998 Schwindemann et al. ...... 556/470

OTHER PUBLICATIONS

Adolfsson et al., "Chiral Lewis acid catalyzed asymmetric nucleophilic ring opening of cyclohexene oxide", *Tetrahedron:Asymmetry*(1995), 6(8), pp. 2023–2031, Jun. 1995.*

Adolfsson, Hans et al., Chiral Lewis Acid Catalysed Asymmetric Nucleophilic Ring Opening of Cyclohexene Oxide, *Tetrahedron: Asymmetry*, 6, 2023–2031, 1995.

Martinez, Luis E. et al., Highly Enantioselective Ring Opening of Epoxides Catalyzed by (salen)Cr(III) Complexes, *J. Am. Chem. Soc.*, 117, 5897–5898, 1995.

Nugent, William A., Chiral Lewis Acid Catalysis. Enantioselective Addition of Azide to Meso Epoxides, *J. Am. Chem. Soc.*, 114, 2768–2769, 1992.

Iida, Takehiko et al., New Asymmetric Reactions Using a Gallium Complex: A Highly Enantioselective Ring Opening of Epoxides with Thiols Catalyzed by a Gallium–Lithium–Bis(binaphthoxide) Complex, *J. Am. Chem. Soc.*, 119, 4783–4784, 1997.

* cited by examiner

*Primary Examiner*—Paul F. Shaver

(57) ABSTRACT

A process for the production of optically active Si compounds by reacting a meso-epoxide with a azidotrimethylsilane and a hydrocarbyl halide in the presence of a catalyst formed from the sequential treatment of hafnium t-butoxide or zirconium t-butoxide with one equivalent of homochiral optically active triisopropanolamine, water, and a source of trifluoroacetae ion is disclosed.

7 Claims, No Drawings

MANUFACTURE OF OPTICALLY ACTIVE HALOHYDRIN TRIALKYLSILYL ETHERS

This application is a 371 of PCT U.S. application Ser. No. 98/14068 filed Jul. 8, 1998 which claims benefit of application U.S. Ser. No. 60/052,196 filed Jul. 10, 1997.

FIELD OF INVENTION

The invention generally relates to the preparation of optically active β-halohydrins protected as their trimethylsilyl ethers using enantioselective Lewis acid catalyst complexes of zirconium or hafnium. The complexes comprise an alkoxide of Hf(IV) or Zr(IV) and an optically active triisopropanolamine.

BACKGROUND OF THE INVENTION

One of the principal goals of modern organic chemistry is the development of new synthetic routes toward the controlled, efficient production of asymmetric compounds. Saturated carbon atoms, which constitute the backbone of most organic compounds, are attached to adjacent atoms through a tetrahedral arrangement of chemical bonds. If the four bonds are to different atoms or groups, the central carbon provides a chiral, or asymmetric center, and the compound therefore may have the ability to exist in two mirror-image, or enantiomeric forms. When synthetic organic chemists attempt preparation of these asymmetric compounds it is crucial to have a means to produce the desired enantiomer because compounds of the wrong enantiomeric form often lack the desired biological, physical or chemical properties. The present invention provides a new process for the synthesis of compounds in a desired enantiomeric form.

An attractive route to such optically active compounds is the enantioselective opening of meso-epoxides with nucleophiles. This procedure is highly efficient because it simultaneously establishes the absolute stereochemistry on two adjacent carbon atoms and results in a useful bifunctional product. An especially attractive version of these reactions involves the use of an enantioselective catalyst to control the position of attack by the nucleophile. In such cases a small amount of a chiral catalyst can be used to produce a large amount of enantiopure product. Prior to the Applicant's discovery, only three catalysts seem to have been reported which promote such reactions in highly enantioselective (>90% enantiomeric excess) fashion. In two cases, the nucleophile is azide (Nugent, William, J. Am. Chem. Soc., 1992, 114, 2768; Martinez, Luis et al., J. Am. Chem. Soc., 1995, 117, 5897). In the remaining case, the nucleophile is t-butyl thiol (Iida, Takehiko et al., J. Am. Chem. Soc., 1997, 119, 4783). To the Applicant's knowledge, there have, however, been no reports of catalysts which promote the enantioselective addition of halides (e.g., Cl, Br, I) to meso-epoxides.

A general review of enantioselective ring opening of meso-epoxides is provided in Hodgson, D. M. Gibbs, A. R.: Lee G. P., Tetrahedron 1996, 52, 46, 14361. One report discloses the use of halodiisopinocamphenylboranes to prepare enantiopure halohydrins [Srebnik M.; Joshi. N. N.; Brown, H. C.; Israel J. of Chem. 1989, 29, 229]. This reaction however, is not catalytic but, rather. stoichiometric. Chiral trivalent aluminum compounds and aluminum chelates were also used to convert meso-epoxides to the chlorohydrin, but low enantiomeric excess was achieved in the stoichiometric process [Naruse, et al; Tetrahedron. 1988, 44, 15, 4747].

Clearly, there is a need to provide a catalytic process for the manufacture of optically active halohydrins as their trimethylsilyl esters. Other objects and advantages of the invention will become apparent to those skilled in the art upon reference to the detailed description which hereinafter follows.

SUMMARY OF THE INVENTION

The present invention provides a process for the manufacture of optically active compounds comprising:

reacting a meso-epoxide with azidotrimethylsilane and a compound of the formula R'X, where R' is an optionally substituted hydrocarbyl and X is selected from the group consisting of Cl, Br, and I;

to produce a compound of the formula (1)

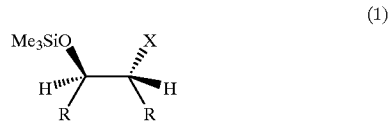

wherein:

R is an optionally substituted hydrocarbyl, or both together can form a ring;

in the presence of a catalytic amount of a catalyst formed from the sequential treatment of hafnium t-butoxide or zirconium t-butoxide with one equivalent of homochiral optically active triisopropanolamine, water and a source of trifluoroacetate ion.

DETAILED DESCRIPTION OF THE PREFERRED EMBODIMENTS

The following definitions are used herein:

The term "hydrocarbyl" means all alkyl, aryl, aralkyl or alkylaryl carbon substituents, either straight-chain, branched or cyclic.

The term "chiral", means "existing as a pair of enantiomers". These stereoisomers, designated the R and S isomers, are mirror images of one another. A chiral material may either contain an equal amount of the R and S isomers in which case it is called "racemic" or it may contain inequivalent amounts of R and S isomer in which case it is called "optically active".

The term "optically active", means a compound which contains inequivalent amounts of the R and S enantiomers. The extent of this inequivalence is measured as the "enantiomeric excess".

The term "enantiomeric excess", means the difference between the percent of R enantiomer and the percent of S enantiomer of an optically active compound. For example, a compound which contains 75% S isomer and 25% R isomer will have an enantiomeric excess of 50%.

The term "enantioselective" means the ability to produce a product in an optically active form.

The term "Me", as used in the equations or formulas, means a methyl group.

The term "meso-epoxide" means an epoxide which contains a mirror plane bisecting the epoxide oxygen atom such that one half of the molecule represents the mirror image of the other half.

The Applicant has discovered a method of using a previously known chiral Lewis acid catalyst to prepare optically active β-halohydrins protected as their trimethylsilyl ethers from the corresponding epoxides. Optically active β-halohydrins are important intermediates in many biologically active compounds (e.g., enantiopure cis-vicinal aminoalcohols including carbocyclic nucleoside antiviral agents). After base induced elimination, the halohydrins can also afford enantiopure cyclopentanones which are intermediates to pharaceutically important prostaglandins.

The general reaction can be described as follows:

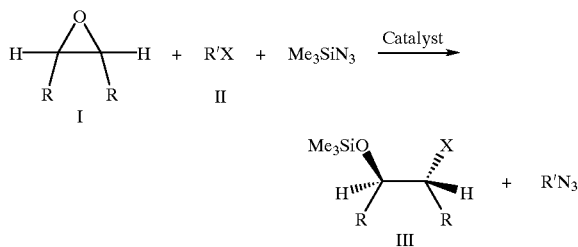

where
R is an optionally substituted hydrocarbyl, or both together can form a ring;
R' is an optionally substituted hydrocarbyl; and
X is Cl, Br, or I.

Compound I can be any cyclic or acyclic meso-epoxide which may additionally contain other substiuents, for example halide or oxygen functionalities such as, but not limited to, ether, ester, and acetal. The epoxide can be part of a larger ring system. Examples of suitable meso-epoxides include, but are not limited to, 1,5-cyclooctadiene monoepoxide, cycloheptene oxide, 1,4-cyclohexadiene monoepoxide, 3,4-epoxy-2,5-dihydrofuran, cyclopentene oxide, cis-2-butene oxide, and trans-1,2-epoxy-4-(methoxymethyl)cyclopentane. Most preferred are cyclopentene oxide and 4-substituted cyclopentene oxide.

Compound II can be any reactive organic halide where X is selected from the group consisting of Cl, Br, and I. R' is any optionally substituted hydrocarbyl. Examples of suitable R'X compounds include, but are not limited to, allyl bromide, allyl iodide, and 2,3-dichloro-1-propene, 3-bromo-2-methylpropene, and benzyl bromide. Preferably, R'X should be selected so that the coproduct $R'N_3$ boils at less than about 150° C. thus facilitating product isolation. Most preferred are allyl bromide and allyl iodide.

The procedure involves treatment of a meso-epoxide in an aprotic organic solvent with from about 1 to 2 molar equivalents of azidotrimethylsilane (preferably about 1.1 molar equivalent) and from about 1.1 to 100 molar equivalents of a reactive organic halide (preferably about 2 to 20 molar equivalents) in the presence of about 0.01 to 0.20 molar equivalents (preferably about 0.08 molar equivalents) of the zirconium or hafnium catalyst.

The reaction may be carried out between about –25° C. and 50° C., preferably at between about 0° C. and 25° C. It is, however, most convenient to carry out the reaction at ambient temperature and pressure.

Suitable solvents for the reaction include aprotic organic solvents, such as chlorobenzene, dichloromethane, 1,2-dichloroethane, ethyl acetate, and toluene. Alternatively, an excess of the reactive organic halide may be used as solvent; for example, neat iodomethane or allyl bromide.

The catalyst utilized can be the particular composition disclosed in U.S. Pat. No. 5,231,203 (Nugent), hereby incorporated by reference. This composition is formed from the sequential treatment of zirconium or hafnium t-butoxide with one equivalent of optically acitve triisopropanolamine, followed by water and then a source of trifluoroacetate ion (including, but not limited to, trimethysilyl trifluoroacetate or aqueous trifluoroacetic acid). Preferred triisopropanolamines are (S,S,S)- or (R,R,R)-triisopropanolamine.

Catalyst preparation is preferably carried out in an aprotic organic solvent. Both the starting metal alkoxide and the alkanolamine ligands should be soluble in the solvent. A solvent with a low-boiling point (less than about 150° C.) is preferred to facilitate catalyst isolation. Examples of suitable solvents include, but are not limited to, tetrahydrofuran, diethyl ether, benzene, toluene, dichloro-methane, 1,2-dichloroethane and the mixtures thereof.

Catalyst preparation involves the reaction of a monomeric zirconium (IV) or hafnium (IV) alkoxide, preferably zirconium (IV) tert-butoxide, with about 1 equivalent of triisopropanolamine. The resultant complex is then treated with about 0.1 to 10 molar equivalents (preferably about 1.0 equivalents) of water. After removal of volatiles by distillation, the complex is treated with about 0.1 to 5 molar equivalents (preferably 0.5 molar equivalents) of trifluoroacetate. Suitable sources of trifluoroacetate include, but are not limited to, trimethylsilyl trifluoroacetate and 50% aqueous trifluoroacetic acid. Preferred conditions for this step involve treatment with trimethylsilyl trifluoroacetate in hexane since the catalyst precipitates from solution as a white solid and may be collected by filtration and optionally dried in high vacuum.

The products of the invention can easily be converted to chiral intermediates useful in the manufacture of pharmaceuticals. The trimethylsilyl ether group can be converted to the corresponding alcohol using methods well known in the art, such as acid hydrolysis. Additionally, the halide substituent could undergo nucleophilic displacement reactions with, for example, azide, cyanide, or thiolate, to afford cis-substituted cycloalkanols. Alternatively, treatment with base affords the corresponding unsaturated derivatives via dehydrohalogenation.

Although the Applicant contemplates many possible uses for the products of the instant invention, one possible example reaction scheme could be illustrated as follows:

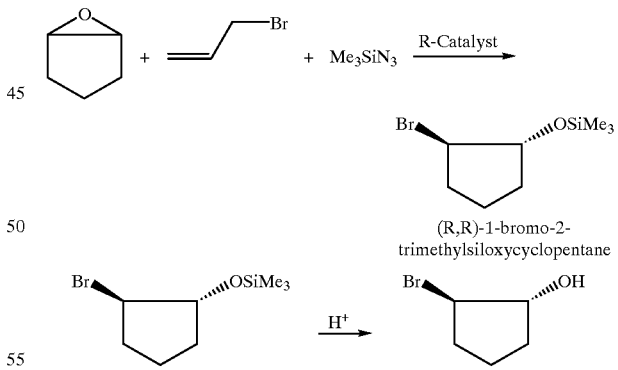

wherein the R-catalyst would be prepared using (R,R,R)-triisopropanolamine as a starting material, as shown below.

Materials and Methods (R)-Propylene oxide, used to prepare (R,R,R)-triisopropanolamine, was purchased from Fluka Chemical Company, Ronkonkoma, N.Y. Zirconium (IV) tert-butoxide was purchased from Strem Chemical Co., Newburyport, Mass. (S)-Propylene oxide and all other organic starting materials were purchased from the Aldrich Chemical Co., Milwaukee, Wis. The meso-epoxides were commercial samples or were prepared by routine oxidation of the corresponding cycloolefins using 3-chloroperoxybenzoic acid. The Cyclodex B® capillary GC column used to determine enantiomeric excess was purchased from J&W Scientific, Folsom, Calif.

EXAMPLES

The following non-limiting examples are intended to further illustrate the invention. All appropriate percentages are by weight unless otherwise noted.

EXAMPLE 1

(R)-Catalyst was prepared as follows. A solution of (R,R,R)-triisopropanolamine (2.43 g, mmol) in dry tetrahydrofuran (15 mL) was added to a solution of zirconium(IV) tert-butoxide (4.86 g, mmol) in 20 mL additional dry THF. After 5 min. the THF was distilled off at reduced pressure. Hexanes (15 mL) were added and distilled off to aid in removing the last traces of side-product tert-butyl alcohol. The residue was redissolved in THF (20 mL) and water (250 mL) was added over the course of several minutes. After 1 h the solvent was distilled away again assisted by addition and removal of hexanes (15 mL). The residue was taken up in hexanes (40 mL). After filtration, trimethylsilyl trifluoroacetate (710 mL) was added to the hexane. After 1 h the precipitated white solid was collected by filtration and dried in high vacuum to afford the (R)-catalyst (1.93 g).

To a vial containing 0.03 grams of (R)-catalyst was added a solution of azidotrimethylsilane (0.34 g, 2.95 mmol) and 1,5-cyclooctadiene monoepoxide (0.30 g, 2.42 mmol) in a mixture of allyl bromide (4.0 mL) and chlorobenzene (4.0 mL). After 48 h the volatiles were removed at reduced pressure and the residue was purified by flash chromatography on 220–400 mesh silica with 98% hexane and 2% ether as eluant. The product (1R,2R)-1-bromo-2-trimethylsiloxycyclooct-5-ene (0.48 g, 72%) was isolated by distillation of the solvent at reduced pressure. Anal. for $C_{11}H_{21}OSiBr$: Calcd: C, 47.65; H, 7.63; Br, 28.82; found: C, 47.84; H, 7.98; Br, 28.95. $^1H$ NMR: d 0.15 (s, 9 H), 1.45–1.89 (m, 8 H), 2.03 (m, 1 H), 2.28 (m, 1 H), 4.01 (m, 1 H),4.12 (m, 1 H). $^{13}C$ NMR: d 0.42, 23.50, 25.42, 33.57, 34.15, 61.54, 75.97, 126.99, 129.75. $[a]_D^{25}$=−14.2, c=1.18 g/100 mL chloroform. Chiral capillary gas chromatographic analysis at 130° C. on Cyclodex B stationary phase (J&W Scientific) indicated that the enantiomeric excess of the product was 79%.

Following the same procedure, a separate reaction was carried out again using 0.03 grams of zirconium catalyst but with diminished amounts of the other reactants as follows: azidotrimethylsilane (0.17 g), 1,5-cyclooctadiene monoepoxide (0.15 g), allyl bromide (2.0 mL), chlorobenzene (2.0 mL). In this case gas chromatographic analysis indicated the product was formed in 85% enantiomeric excess.

EXAMPLE 2

To a vial containing 0.03 grams of (R)-catalyst prepared as in Example 1 was added a solution of azidotrimethylsilane (0.34 g, 2.95 mmol) and cycloheptene oxide (0.28 g, 2.50 mmol) in a mixture of allyl bromide (4.0 mL) and chlorobenzene (4.0 ml). After 48 h the volatiles were removed at reduced pressure and the residue was purified by flash chromatography on 220–400 mesh silica with 98% hexane and 2% ether as eluant. The product (1R,2R)-1-bromo-2-trimethylsiloxycycloheptane (0.54 g, 82%) was isolated by distillation of the solvent at reduced pressure. Anal. for $C_{10}H_{21}OSiBr$. Calcd: C, 45.28; H, 7.98; Br. 30.12; found: C, 45.26; H, 8.12; Br 30.55. $^1H$ NMR: d 0.17 (s, 9 H), 1.45–1.89 (m, 8 H), 2.03 (M, 1 H), 2.28 (m, 1 H), 4.01 (m, 1 H), 4.12 (m, 1 H). $^{13}C$ NMR: d 0.33, 21.62, 24.26, 27.49, 33.78, 34.13, 62.41, 78.90. $[a]_D^{25}$=−28.2, c=1.24 g/100 mL chloroform. Chiral capillary gas chromatographic analysis at 120° C. on Cyclodex B stationary phase indicated that the enantiomeric excess of the product was 80%.

Following the same procedure, a separate reaction was carried out again using 0.03 grams of zirconium catalyst but with diminished amounts of the other reactants as follows: azidotrimethylsilane (0.17 g), cycloheptene oxide (0.14 g), allyl bromide (2.0 mL), chlorobenzene (2.0 mL). In this case gas chromatographic analysis indicated the product was formed in 88% enantiomeric excess.

EXAMPLE 3

To a vial containing 0.03 grams of (R)-catalyst prepared as in Example 1 was added a solution of azidotrimethylsilane (0.34 g, 2.95 mmol) and 1,4-cyclohexadiene monoepoxide (0.24 g, 2.50 mmol) in a mixture of allyl bromide (4.0 mL) and chlorobenzene (4.0 mL). After 48 h the volatiles were removed at reduced pressure and the residue was purified by flash chromatography on 220–400 mesh silica with 98% hexane and 2% ether as eluant. The product (1R,2R)-1-bromo-2-trimethylsiloxycyclohex-4ene (0.56 g, 90%) was isolated by distillation of the solvent at reduced pressure. Anal. for $C_9H_{17}OSiBr$. $^1H$ NMR: d 0.16 (s, 9 H), 2.12 (m, 1 H), 2.48–2.59 (m, 2 H), 2.86 (m, 1 H), 3.94 (m, 1 H), 4.07 (m, 1 H), 5.49 (m, 1 H), 5.59 (m, 1 H). $^{13}C$ NMR: d 0.27, 33.96, 34.63, 52.99, 70.83, 124.17, 124.40. $[a]_D^{25}$=−85.3, c=0.31 g/100 mL chloroform. Chiral capillary gas chromatographic analysis at 110° C. on Cyclodex B stationary phase indicated that the enantiomeric excess of the product was 79%.

Following the same procedure, a separate reaction was carried out again using 0.03 grams of zirconium catalyst but with diminished amounts of the other reactants as follows: azidotrimethylsilane (0.17 g), 1,4-cyclohexadiene monoepoxide (0.12 g), allyl bromide (2.0 mL). chlorobenzene (2.0 mL). In this case gas chromatographic analysis indicated the product was formed in 92% enantiomeric excess.

EXAMPLE 4

(S)-Catalyst was prepared as follows. A solution of (S,S,S)-triisopropanolamine (3.40 g, mmol) in dry tetrahydrofuran (15 mL) was added to a solution of zirconium(IV) tert-butoxide (6.80 g, mmol) in additional dry THF (25 mL). After 5 min. the THF was distilled off at reduced pressure. Hexanes (15 mL) were added and distilled off to aid in removing the last traces of side-product tert-butyl alcohol. The residue was redissolved in THF (25 mL) and water (350 mL) was added over the course of several minutes. After 1 h the solvent was distilled away again assisted by addition and removal of hexanes (15 mL). The residue was taken up in hexanes (40 mL). After filtration, trimethylsilyl trifluoroacetate (1.00 mL) was added to the hexane. After 1 h the precipitated white solid was collected by filtration and dried in high vacuum to afford the (S)-catalyst (2.45 g).

To a vial containing 0.03 grams of this (S)-catalyst was added a solution of azidotrimethylsilane (0.34 g, 2.95 mmol) and cyclohexene oxide (0.24 g, 2.45 mmol) in a mixture of allyl bromide (4.0 mL) and chlorobenzene (4.0 mL). After 48 h the volatiles were removed at reduced pressure and the residue was purified by flash chromatography on 220–400 mesh silica with 98% hexane and 2% ether as eluant. The product (1S,2S)-1-bromo-2-trimethysiloxycyclohexane (0.44 g, 71%) was isolated by distillation of the solvent at reduced pressure. Anal. for $C_9H_{19}OSiBr$: Calcd: C, 43.03; H, 7.62; Br, 31.80; found: C, 43.06; H, 7.69; Br, 31.78. $^1H$ NMR: d 0.19 (s, 9 H), 1.24–1.46 (m, 3 H), 1.64–1.87 (m, 3 H), 2.01 (m, 1 H), 2.35 (m, 1 H), 3.66 (m, 1 H), 3.87 (m, 1 H). $^{13}C$ NMR: d 24.15, 25.70, 34.96, 35.62, 58.44, 75.38. $[a]_D^{25}$=+39.0, c=1.02 g/100 mL chloroform. Chiral capillary gas chromatographic analysis at 120° C. on Cyclodex B stationary phase indicated that the enantiomeric excess of the product was 85%.

Following the same procedure, a separate reaction was carried out again using 0.03 grams of zirconium catalyst but with diminished amounts of the other reactants as follows: azidotrimethylsilane (0.17 g), cyclohexene oxide (0.12 g), allyl bromide (2.0 mL), chlorobenzene (2.0 mL). In this case gas chromatographic analysis indicated the product was formed in 91% enantiomeric excess.

An additional reaction was carried out as in the preceding example except that the mixture was maintained in a refrigerator at 4° C. for 8 days after mixing. The enantiomeric excess of the product in this case was 94%.

EXAMPLE 5

To a vial containing 0.03 grams of (S)-catalyst prepared as in Example 4 was added a solution of azidotrimethylsilane (0.17 g, 1.47 mmol) and 3,4-epoxy-2,5-dihydrofuran (0.12 g, 1.39 mmol) in a mixture of allyl bromide (2.0 mL) and chlorobenzene (2.0 mL). Chiral gas chromatographic analysis at 110° C. on a Cyclodex B stationary phase indicated that the product (3S,4S)-3-bromo4-trimethylsiloxy-2,5-dihydrofuran had formed in 67% enantiomeric excess.

EXAMPLE 6

To a vial containing 0.03 grams of (S)-catalyst prepared as in Example 4 was added a solution of azidotrimethylsilane (0.17 g, 1.47 mmol) and cyclopentene oxide (0.10 g, 1.19 mmol) in a mixture of allyl bromide (2.0 mL) and chlorobenzene (2.0 mL). Chiral gas chromatographic analysis at 110° C. on a Cyclodex B stationary phase indicated that the product (1S,2S)-1-bromo-2-trimethylsiloxycyclopentane had formed in 95% enantiomeric excess.

EXAMPLE 7

To a vial containing 0.03 grams of (S)-catalyst prepared as in Example 4 was added a solution of azidotrimethylsilane (0.17 g, 1.47 mmol) and cis-2-butene oxide(0.09 g, 1.25 mmol) in a mixture of allyl bromide (2.0 mL) and chlorobenzene (2.0 mL). Chiral gas chromatographic analysis at 55° C. on a Cyclodex B stationary phase indicated that the product (2S,3S)-2-bromo-3-trimethylsiloxybutane had formed in approximately 85% enantiomeric excess.

EXAMPLE 8

To a vial containing 0.03 grams of (S)-catalyst prepared as in Example 4 was added a solution of azidotrimethylsilane (0.17 g, 1.47 mmol) and trans-1,2-epoxy-4-(methoxymethyl)cyclopentane (0.16 g, 1.25 mmol) in a mixture of allyl bromide (2.0 mL) and chlorobenzene (2.0 mL). Chiral gas chromatographic analysis at 110° C. on a Cyclodex B stationary phase indicated that the product (1S,2S,4S)-1-bromo-2-trimethylsiloxy-4-(methoxymethyl)cyclopentane had formed in 95% enantiomeric excess.

EXAMPLE 9

To a vial containing 0.03 grams of (S)-catalyst prepared as in Example 4 was added a solution of azidotrimethylsilane (0.17 g, 1.47 mmol) and ethyl trans-1,2-epoxy-4-cyclopentanecarboxylate (0.19 g, 1.23 mmol) in allyl bromide (2.0 mL) and chlorobenzene (2.0 mL). After 48 h the volatiles were removed at reduced pressure and the residue was purified by flash chromatography on 220–400 mesh silica with 90% hexane and 10% ether as eluant. The product (1S,2S,4S)-1-bromo-1-trimethylsiloxy-4-carboxylic acid ethyl ester (0.29 g, 77%) was isolated by distillation of the solvent. Anal. for $C_{11}H_{21}O_3SiBr$. Calcd: C, 42.72; H, 6.84; Br, 25.84. Found: C, 43.74; H, 6.99; Br, 25.93. $^1H$ NMR ($CDCl_3$/TMS): δ 0.13 (s, 9 H), 1.27 (t, J=7, 3 H), 1.86 (m, 1 H), 2.30 (m, 1 H), 2.39 (m, 1 H), 2.70 (m, 1 H), 3.04 (m, 1 H), 3.96 (m, 1 H), 4.16 (q, J=7, 2 H), 4.33 (m, 1 H). $^{13}C$ NMR ($CDCl_3$/TMS): δ 0.00, 14.16, 35.72, 37.33, 40.51, 54.28, 60.75, 80.06, 174.80. $[a]_D^{25}$=−38.8°, c=1.04 g/100 mL chloroform.

EXAMPLE 10

To a vial containing 0.03 grams of (S)-catalyst prepared as in Example 4 was added a solution of azidotrimethylsilane (0.17 g, 1.47 mmol), cyclopentene oxide (0.10 g, 1.19 mmol), and allyl iodide (0.41 g, 2.44 mmol) in chlorobenzene (3.0 mL). After 48 h the volatiles were removed at reduced pressure and the residue was purified by flash chromatography on 220–400 mesh silica with 98% hexane and 2% ether as eluant. The product (1S,2S)-1-iodo-2-trimethylsiloxycyclopentane (0.22 g, 75%) was isolated by distillation of the solvent. Anal. for $C_8H_{17}OSiI$. Calcd: C, 33.81; H, 6.03; 1, 44.65. Found: C, 34.60; H. 5.79; I, 44.21. $^1$ H NMR ($CDCl_3$/TMS): δ 0.13 (s, 9 H), 1.53 (m, 1 H), 1.77 (m, 2 H), 1.97–2.12 (m, 2 H), 2.32 (m, 1 H), 4.01 (m, 1 H), 4.42 (m, 1 H). $^{13}C$ NMR ($CDCl_3$/TMS): δ 0.11, 22.37, 32.35, 34.64, 35.96, 82.48. $[a]_D^{25}$=+86.4°, c=1.04 g/100 mL chloroform. Chiral capillary gas chromatographic analysis at 110° C. on Cyclodex B stationary phase indicated that the enantiomeric excess of the product was 95%.

EXAMPLE 11

To a vial containing 0.03 grams of (S)-catalyst prepared as in Example 4 was added a solution of azidotrimethylsilane (0.17 g, 1.47 mmol) and cyclopentene oxide (0.10 g, 1.19 mmol) in 2,3-dichloro-1-propene (3.0 mL). After 48 h the solution was analyzed by chiral capillary gas chromatography at 100° C. on Cyclodex B stationary phase which showed, in addition to the azide adduct (1S,2S)-1-azido-2-trimethylsiloxycyclopentane (33% of product, 71% ee), the chloride adduct (1S,2S)-1-chloro-2-trimethylsiloxycyclopentane (67% of product, 91% ee). The retention time for the two enantiomers of the chloride adduct were 5.3 minutes (minor) and 5.5 minutes (major).

In a separate experiment 0.03 grams of the (R)-catalyst prepared as in Example 4 was dissolved in the same solution as above. The major and minor peaks for the chloride adduct had now reversed indicating formation of the (1R,2R) stereoisomer. The enantiomeric excess for this reaction was again 91%.

EXAMPLE 12

To a vial containing 0.03 grams of (S) catalyst prepared as in Example 4 was added a solution of azidotrimethylsilane (0.17 g, 1.47 mmol) and trans-4-methoxy-1,2-epoxycyclopentane (0.14 g, 1.23 mmol) in allyl bromide (2.0 mL) and chlorobenzene (2.0 mL). After 48 h the solution was analyzed by chiral capillary gas chromatography at 115° C. on Cyclodex B stationary phase which showed that the product (1S,2S, 4S)-1-bromo-2- trimethylsiloxy-4-methoxycyclopentane was formed in 96% enantiomeric excess. The retention time for the two enantiomers of the product were 13.4 minutes (minor) and 13.6 minutes (major).

In a separate experiment 0.03 grams of the (R)-catalyst prepared as in Example 4 was dissolved in the same solution as above. The major and minor peaks for the product enantiomers had now reversed indicating predominant formation of the (1R,2R,4R) stereoisomer. The enantiomeric excess for this reaction was again 96%.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for the manufacture of optically active compounds comprising:

reacting a meso-epoxide with azidotrimethylsilane and a compound of the formula R'X, where R' is an optionally substituted hydrocarbyl and X is selected from the group consisting of Cl, Br and I;

to produce a compound of the formula (1)

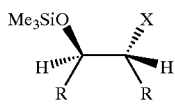

(1)

wherein:

R is optionally substituted hydrocarbyl, or both together can form a ring;

in the presence of a catalytic amount of a catalyst formed from the sequential treatment of hafnium t-butoxide or zirconium t-butoxide with one equivalent of homochiral optically active triisopropanolamine, water and a source of trifluoroacetate ion.

2. The process of claim 1, wherein the optically active triisopropanolamine is selected from the group consisting of (S,S,S)-triisopropanolamine and (R,R,R)-triisopropanolamine.

3. The process of claim 1 wherein R'X is selected from the group consisting of allyl bromide, allyl iodide, and 2,3-dichloro-1-propene.

4. The process of claim 1 wherein the meso-epoxide is selected from the group consisting of 1,5-cyclooctadiene monoepoxide, cycloheptene oxide, cyclohexadiene monoepoxide, 3,4-epoxy-2,5-dihydrofuran, cyclopentene oxide, cis-2-butene oxide, and trans-1,2-epoxy-4-(methoxymethyl)cyclopentane.

5. The process of claim 1 wherein the compound of Formula (1) exhibits optical activity to the extent of greater than about 50% enantiomeric excess.

6. The process of claim 1 wherein the compound of Formula (1) exhibits optical activity to the extent of greater than about 75% enantiomeric excess.

7. The process of claim 1 wherein the catalyst is formed from zirconium t-butoxide.

* * * * *